United States Patent [19]

Ort

[11] 4,400,554

[45] Aug. 23, 1983

[54] PROCESS FOR MAKING BIS(HYDROXYPHENYL)METHANES

[75] Inventor: Morris R. Ort, Wilbraham, Mass.

[73] Assignee: Monsanto Company, St. Louis, Mo.

[21] Appl. No.: 362,719

[22] Filed: Mar. 29, 1982

[51] Int. Cl.³ .............................................. C07C 39/16
[52] U.S. Cl. ..................................... 568/727; 568/728
[58] Field of Search ................................. 568/727, 728

[56] References Cited

U.S. PATENT DOCUMENTS 2,812,364  11/1957  Farnham et al. .................... 568/727

FOREIGN PATENT DOCUMENTS

| 1135488 | 8/1962 | Fed. Rep. of Germany | 568/727 |
| 1135489 | 8/1962 | Fed. Rep. of Germany | 568/727 |
| 2419820 | 11/1974 | Fed. Rep. of Germany | 568/727 |
| 2418975 | 10/1975 | Fed. Rep. of Germany | 568/727 |
| 40-16538 | 7/1965 | Japan | 568/727 |
| 42-2350 | 2/1967 | Japan | 568/727 |

OTHER PUBLICATIONS

"Hackh's Chemical Dictionary" 3rd Ed. (1944) McGraw-Hill pub., p. 649.

*Primary Examiner*—Werren B. Lone
*Attorney, Agent, or Firm*—R. Bruce Blance; William J. Farrington; Paul D. Matukaitis

[57] ABSTRACT

Bis(hydroxyphenyl)methanes are prepared by reaction of phenol and formaldehyde in a two-phase mixture containing aqueous phosphoric acid. The reaction conditions can be selected to provide high yields of bis(hydroxyphenyl)methanes or to yield bis(hydroxyphenyl)methanes containing a high concentration of the 4,4'-isomer.

13 Claims, No Drawings

PROCESS FOR MAKING BIS(HYDROXYPHENYL)METHANES

This invention relates to a process for the preparation of bis(hydroxyphenyl)methanes by the reaction of phenol and formaldehyde in the presence of aqueous phosphoric acid.

Heretofore, the preparation of bis(hydroxyphenyl)methanes has been carried out by reaction of phenol and formaldehyde in the presence of strong mineral acids such as hydrochloric and sulfuric acids. Hydrochloric acid catalyzed processes suffer from several disadvantages: the volatility of hydrogen chloride gas; the corrosiveness of hydrochloric acid; the tendency to produce chloromethyl ether and chloromethylphenols; and the use of relatively dilute acid which makes separation of the aqueous and organic phases and recycle of the acid phase difficult. Sulfuric acid processes are undesirable for several reasons including: the tendency to form sulfonated products, generating severe discoloration of the reaction products and making separation of the aqueous and organic phases difficult; the need for dilute acid solutions to minimize sulfonation; and the requirement of high ratios of acid to phenol to obtain high concentrations of diphenol in the reaction product.

I have now found that the use of phosphoric acid as the catalyst provides a process for the preparation of bis(hydroxyphenyl)methanes of improved color, and in high yield, in which the ratio of phenol to acid catalysts is substantially higher than in other catalyzed processes. Surprisingly the low solubility of phenol in phosphoric acid and conversely of phosphoric acid in phenol does not impair the reaction rate but greatly aids product separation and catalyst recycle.

In the process, phenol and formaldehyde are reacted in a two phase mixture containing at least about 3 moles of phenol per mole of formaldehyde and an aqueous solution of phosphoric acid containing not more than about 2 mole of phosphoric acid per mole of phenol and from about 1.5 to about 6.0 moles of water per mole of phosphoric acid to produce bis(hydroxyphenyl)methanes and the organic phase containing the reaction product comprising bis(hydroxyphenyl)methanes is separated from the aqueous phase. Advantageously the mole ratio of phenol to formaldehyde is in the range of about 3 to about 20, the mole ratio of phenol to phosphoric acid is in the range of about 0.5 to about 8 and the mole ratio of water to phosphoric acid is in the range of about 1.5 to about 6. The preferred mole ratios are in the following respective ranges about 4 to about 6; about 2 to about 4 and about 2.5 to about 3.0.

A high ratio of phenol to formaldehyde minimizes by-product formation but greater energy consumption is caused by the greater load of recycled unreacted phenol. Similarly a higher acid ratio gives a faster reaction rate but increases the energy consumption because of the greater load of recycled acid. Indeed it is an advantage of the present process that phenol to acid mole ratios in the range of about 2 to about 4 give a high yield in the range of about 90 percent of bis(hydroxyphenyl)methanes. Water plays a significant role in the reaction, affecting both the yield of bis(hydroxyphenyl)methanes and the selectivity. The amount of water depends to some extent on the reaction temperature and the acid catalyst ratio.

In the reaction of phenol and formaldehyde, the first step is the addition of formaldehyde to phenol to form a mixture of about 60 percent 4-(hydroxymethyl)phenol and 40 percent 2-(hydroxymethyl)phenol.

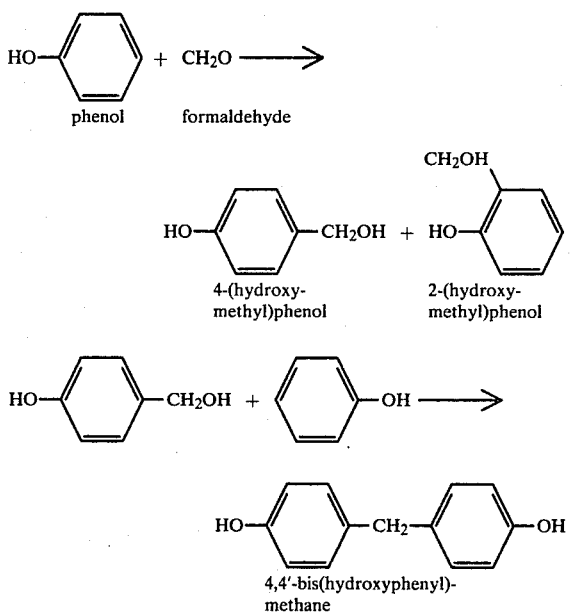

The most noticeable effect of water is the inhibition of the reaction of 2-(hydroxymethyl)phenol and phenol with the result that the formation of a predominant amount of 4,4'-bis(hydroxyphenyl)methane, a minor amount of the 2,4'-isomer and a negligible amount of the 2,2'-isomer occurs. It is believed that because the reaction of 2-(hydroxymethyl)phenol with phenol and with bis(hydroxyphenyl)methanes is inhibited, 2-(hydroxymethyl)phenol tends to react with more formaldehyde forming 2,4- and 2,6-dihydroxymethylphenols which then form oligomers. With adjustment of the reaction conditions the 4,4'-bis(hydroxyphenyl)methane content of the bis(hydroxyphenyl)methane product can be varied in the range of 55 to 75 percent, the oligomeric by-product increasing with the concentration of 4,4'-isomer. Reaction conditions can be selected so that the yield of bis(hydroxyphenyl)methanes based on formaldehyde is at least about 80 percent. Indeed yields of 90 percent have been obtained, with the recovered product containing 92 to 94 weight percent of bis(hydroxyphenyl)methanes of which 55 percent is 4,4'-bis(hydroxyphenyl)methane. When conditions are changed to provide bis(hydroxyphenyl)methanes containing about 75 percent of the 4,4'-isomer, the yield based on formaldehyde is about 68 percent and 74 weight percent of the total product is bis(hydroxyphenyl)methane and 26 weight percent is oligomeric. The mole ratio of water to phenol for good selectivity of the 4,4'-isomer and good yield of bis(hydroxyphenyl)methanes is preferably about 1.0.

Advantageously, when the reaction is carried out, the phenol and aqueous acid are mixed initimately and the formaldehyde is added continuously throughout the reaction so that the instantaneous phenol formaldehyde ratio is much greater than it would be if all the formaldehyde were added initially and the concentration of 2-(hydroxymethyl) phenol is severely limited, preventing the formation of appreciable amounts of oligomer.

Since the ratio of phenol to formaldehyde is always high the rate of addition of formaldehyde can be linear throughout the reaction or can be reduced throughout the reaction.

The reaction can be carried out at any temperature in the range of about 10° C. to about 60° C. If the temperature is below about 40° C. a solvent can be advantageously added to the organic phase to maintain phenol and the bis(hydroxyphenyl)methanes in solution. Suitable solvents include toluene, xylene and dichloromethane. At temperatures above about 60° C., the rate of reaction of 2-(hydroxymethyl)phenol and 4-(hydroxymethyl)phenol with bis(hydroxyphenyl)methanes is increased thus decreasing the yield of bis(hydroxyphenyl)methanes. It is therefore preferable to carry out the reaction at a temperature in the range of about 40° to about 50° C. and more preferably in the range of about 43° to about 47° C.

When the concentration of bis(hydroxyphenyl)methanes rises above approximately 40 weight percent, the 4,4'-isomer may begin to precipitate. Precipitation can, of course, be enhanced at the completion of the reaction by lowering the batch temperature. Separation of the solids by filtration or centrifugation is very difficult and tedious because of the fine particle size of the solids. A stable high viscosity emulsion is formed. Easy separation is achieved by raising the batch temperature, after completion of the reaction, to 65–70° C. to dissolve any solids in the phenol phase. Reduced agitation permits greater coalescence of the dispersed phase. When agitation is then stopped, separation of the two liquid phases is rapid and very complete.

After decantation, it is essential that any residual acid in the phenol phase be neutralized before proceeding to temperature conditions of 100° C. and higher. Otherwise, the bis(hydroxyphenyl)methanes are rapidly degraded to higher molecular weight material (Novolac resins) and phenol. After neutralization, the preferred pH range is 4.5–5.5 (substitution for one acid hydrogen atom). Alkaline pH must be avoided to prevent color development.

To lessen the loss of bis(hydroxyphenyl)methanes and phenol caused by absorption on the filtered or settled salt after neutralization of the phenol phase, it may be necessary to wash the salt with methanol or hot phenol and recover the bis(hydroxyphenyl)methanes from the washings.

The most readily available and lowest cost source of phosphoric acid is 85 percent phosphoric acid but the acid can be obtained from any source such as by dissolving phosphorus pentoxide in water. Formaldehyde is conveniently supplied by formalin solutions, in the range of 37–50 weight percent. However other concentrations and other sources such as trioxane, paraformaldehyde and methylal can be used.

The following examples set forth methods of carrying out the process of the invention but should not be regarded as limitations thereof. Unless otherwise indicated parts and percentages are by weight.

EXAMPLE 1

130 parts of 85% phosphoric acid is added to 265 parts of freshly distilled liquid phenol (F.P. 40.8° C.) in a nitrogen-blanketed, stirred stainless steel reactor and the temperature is adjusted to 45° C. A two-phase mixture is formed and is stirred vigorously to thoroughly disperse the aqueous acid phase. 45.75 parts of 47% formalin is then metered at about 11.4 parts per hour to the reaction mixture over a 4 hr. period. The reaction temperature is controlled at 45±2° C. during the formalin addition and for 30 minutes thereafter. When conversion proceeds to the point where the bis(hydroxyphenyl)methane concentration is about 40% by wt. of the phenol phase, some 4,4' isomer precipitates and the mixture viscosity rapidly changes from about 100 to 1000 cp, and a crystallization exotherm is observed. Formaldehyde conversion to bis(hydroxyphenyl)methanes is about 90% and the resultant isomer ratio is about 55/37/8 4,4'-, 2,4'-, 2,2'-isomers. The remainder of the formaldehyde is converted to higher molecular weight products. At the completion of the reaction, the temperature is raised to 65° C. to dissolve any precipitated solids and the agitator tip speed is reduced by 50%. Batch temp. is maintained at 65° C. for 30 minutes and then the agitation is stopped and the acid and oil phases are allowed to separate. The acid phase is drawn from the bottom of the reactor. 98–99% of the acid is recovered as a 70% aqueous phosphoric acid solution with a specific gravity of 1.5.

Residual acid in the organic phase is partly neutralized by the addition of 4 parts of solid sodium bicarbonate with agitation to provide a pH of about 5.0. Alkaline pH must be avoided to prevent color development. Carbon dioxide evolved in the neutralization is vented to the atmosphere. The sodium dihydrogen phosphate which precipitates is removed by filtering. The viscosity of the organic phase after filtration is about 10 cp. The organic phase is concentrated by removing water and unreacted phenol under vacuum. The temperature is raised to 120° C. and distillation is initiated at about 425 torr. The pot temperature is gradually raised to 140° C. and distillation is continued until the pressure has been reduced to 1 torr. 159 parts of phenol and 13 parts of water are distilled. The residue is about 90% bis(hydroxyphenyl)methane and 10% oligomers. Residue solidification occurs at roughly 120° C. Contact with air is minimized when material is hot to prevent color formation. Distillation of the phenol-stripped material is continued at 1 torr to a pot temperature of 230° C. The distillate comprises 100 parts of bis(hydroxyphenyl)methanes. 4,4'-bis(hydroxyphenyl)methane is the highest melting and boiling isomer. The freezing point of 4,4'-bis(hydroxyphenyl)methane is about 162° C., that of the 2,4'-isomer is 120° C., and that of the 2,2'-isomer is 119° C. The distillate is kept at 160° C. or above to prevent freezing. It can be poured into shallow pans for cooling and crystallizing. Again, contact with air must be prevented as much as possible when the material is hot.

Determination of isomers in the synthesis products is carried out by liquid chromatography in a Waters 6000A liquid chromatograph with U.V. detector (254 nm) and $C_{18}\mu$Bondapak column. The eluant solution consists of 39% freshly distilled tetrahydrofuran, 60% distilled water and 1% acetic acid, degassed and at ambient temperature. The eluant flow rate is 1 ml/min. The analytical sample consists of 1g. of reaction product diluted to 100 ml. with the tetrahydrofuran/water solution.

Several peaks are generally seen in a typical chromatogram. Proper identification of the components of interest is important. The retention time of a peak may be affected by several factors that may differ significantly from chromatograph to chromatograph and from one batch of solvent to the next. Thus, more useful parameters for peak identification must be used. Two of the most useful parameters for peak identification are the retention factor (k) and the relative retention (α).

With phenol as the standard, the relative retention factors are tabulated below for the other peaks.

| COMPONENT | k' | α |
|---|---|---|
| 4-(hydroxymethyl)phenol | .895 | .3131 |
| 2-(hydroxymethyl)phenol | 1.351 | .4726 |
| Phenol | 2.859 | 1.0 |
| 4,4'-bis(hydroxyphenyl)methane | 4.068 | 1.4229 |
| 2,4'-bis(hydroxyphenyl)methane | 4.969 | 1.738 |
| 2,2-bis(hydroxyphenyl)methane | 6.859 | 2.399 |
| Trimer | 5.995 | 2.097 |

EXAMPLE 2

25.7 parts (0.273 mole) of phenol is dissolved in 20 parts of toluene and the solution cooled in a constant temperature bath controlled at 10° C. In a separate vessel 5.8 parts of 37% formalin (0.072 moles $CH_2O$) is added to 16.2 parts of 85% phosphoric acid (0.142 mole $H_3PO_4$) with stirring and the mixture is cooled to 10° C. The phosphoric acid/formalin solution is added to the stirred phenol/toluene solution. The two phase reaction mixture is stirred for about 20 hrs. at 10° C. The reaction mixture is diluted with 40 parts of methyl alcohol giving a homogeneous solution. The reaction mixture is analyzed by liquid chromatography. The yield of bis(hydroxyphenyl)methane based on formaldehyde is about 69% and the isomer ratio is 76.2/22.3/1.4, 4,4'-, 2,4'-, 2,2'-isomers respectively.

What is claimed is:

1. A process for producing bis(hydroxyphenyl)methanes which comprises reacting phenol and formaldehyde at a temperature in the range of about 10 to about 60° C. in a two phase mixture containing at least about 3 moles of phenol per mole of formaldehyde and an aqueous solution of phosphoric acid containing less than about 2 mole of phosphoric acid per mole of phenol and from about 1.5 to about 6.0 moles of water per mole of phosphoric acid to produce bis(hydroxyphenyl)methanes and separating the organic phase containing the bis(hydroxyphenyl)methanes from the aqueous phase.

2. The process of claim 1 wherein the mole ratio of phenol to formaldehyde is in the range of about 3 to about 20, the mole ratio of phenol to phosphoric acid is in the range of about 0.5 to about 8 and the mole ratio of water to phosphoric acid is in the range of about 1.5 to about 6.

3. The process of claim 1 wherein the mole ratio of phenol to formaldehyde is in the range of about 4 to about 6, the mole ratio of phenol to phosphoric acid is in the range of about 2 to about 4 and the mole ratio of water to phosphoric acid is in the range of about 2.5 to about 3.0.

4. The process of claim 1, 2 or 3 wherein the mole ratio of phenol to water is about 1.

5. The process of claim 1, 2 or 3 wherein the separated organic phase is partly neutralized to a pH in the range of about 4.5 to about 5.5, filtered and distilled to provide the bis(hydroxyphenyl)methane fraction.

6. The process of claim 1, 2 or 3 wherein the reaction temperature is in the range of about 40 to about 50° C.

7. The process of claim 1, 2 or 3 wherein the yield of bis(hydroxyphenyl)methanes, based on the formaldehyde reactant is at least about 80 percent.

8. The process of claim 1, 2 or 3 wherein the bis(hydroxyphenyl)methanes contain from about 55 to about 75 percent of the 4,4'-isomer.

9. A two phase process for producing bis(hydroxyphenyl)methanes which comprises forming a dispersion of aqueous phosphoric acid in phenol or in an organic solvent solution of phenol, adding aqueous formaldehyde solution continuously with vigorous agitation to cause rapid dispersion of the aqueous formaldehyde solution in the dispersion at a temperature in the range of about 10° to about 60° C., raising the temperature of the dispersion to 65° to 70° C. to allow precipitated bis(hydroxyphenyl)methane to dissolve in the phenol phase, separating the aqueous phase from the phenol phase, adding base to the phenol phase to raise the pH to about 4.5 to 5.5, filtering off precipitated salt from the phenol phase and distilling the phenol phase to remove unreacted phenol, wherein the mole ratio of phenol reactant to formaldehyde reactant is at least about 3, wherein the mole ratio of phenol reactant to phosphoric acid is at least about 0.5 and wherein the mole ratio of water to phosphoric acid is in the range of about 1.5 to about 6.0.

10. The process of claim 9 wherein the mole ratio of phenol to formaldehyde is in the range of about 4 to about 6, the mole ratio of phenol to phosphoric acid is in the range to about 2 to about 4 and the mole ratio of water to phosphoric acid is in the range of about 2.5 to about 3.0.

11. The process of claim 9 wherein the reaction temperature is in the range of about 40° to about 50° C.

12. The process of claim 9 wherein the yield of bis(hydroxyphenyl)methanes, based on the formaldehyde reactant is at least about 80 percent.

13. The process of claim 9 wherein the bis(hydroxyphenyl)methanes contain from about 55 to about 75 percent of the 4,4'-isomer.

* * * * *